United States Patent [19]
Beckers et al.

[11] Patent Number: 5,888,224
[45] Date of Patent: Mar. 30, 1999

[54] IMPLANT FOR INTERVERTEBRAL SPACE

[75] Inventors: Louis Francois Charles Beckers, Bonheiden, Belgium; Johannes Fridolin Schläpfer, Glarus, Switzerland

[73] Assignee: Synthesis (U.S.A.), Paoli, Pa.

[21] Appl. No.: 926,242

[22] Filed: Sep. 5, 1997

Related U.S. Application Data

[63] Continuation of Ser. No. 436,302, filed as PCT/CH94/00184 Sep. 20, 1994, abandoned.

[30] Foreign Application Priority Data

Sep. 21, 1993 [BE] Belgium ............................. 09300982

[51] Int. Cl.⁶ ........................................................ A61F 2/44
[52] U.S. Cl. ............................................................ 623/17
[58] Field of Search .................................. 606/60, 61, 72, 606/73, 74, 76, 191; 623/11, 16, 17, 18

[56] References Cited

U.S. PATENT DOCUMENTS

| | | |
|---|---|---|
| 3,486,505 | 5/1967 | Morrison . |
| 4,349,921 | 9/1982 | Kuntz . |
| 4,599,086 | 7/1986 | Doty . |
| 4,772,287 | 9/1988 | Ray et al. . |
| 4,834,757 | 5/1989 | Brantigan . |
| 4,863,476 | 9/1989 | Shepperd . |
| 4,878,915 | 11/1989 | Brantigan . |
| 5,015,247 | 5/1991 | Michelson . |
| 5,092,893 | 3/1992 | Smith . |
| 5,171,278 | 12/1992 | Pisharodi . |
| 5,192,327 | 3/1993 | Brantigan ................................. 606/61 |
| 5,306,307 | 4/1994 | Senter et al. . |
| 5,425,772 | 6/1995 | Brantigan ................................. 606/61 |
| 5,443,514 | 8/1995 | Steffee ..................................... 623/17 |
| 5,458,638 | 10/1995 | Kuslich ..................................... 623/17 |
| 5,489,308 | 2/1996 | Kuslich ..................................... 623/17 |
| 5,658,337 | 8/1997 | Kohrs ........................................ 623/17 |

FOREIGN PATENT DOCUMENTS

| | | |
|---|---|---|
| 0 042 271 | 12/1981 | European Pat. Off. ................. 623/17 |
| 0493698 | 8/1992 | European Pat. Off. . |
| 2703580 | 3/1993 | France . |
| 8912431 | 12/1989 | WIPO . |
| 9000037 | 1/1990 | WIPO . |
| WO 93/01771 | 2/1993 | WIPO ..................................... 623/17 |

*Primary Examiner*—Michael J. Milano
*Attorney, Agent, or Firm*—Fish & Richardson P.C.

[57] ABSTRACT

An implant for the intervertebral space consists of an essentially cuboid body with a device for gripping by a tool.

38 Claims, 6 Drawing Sheets

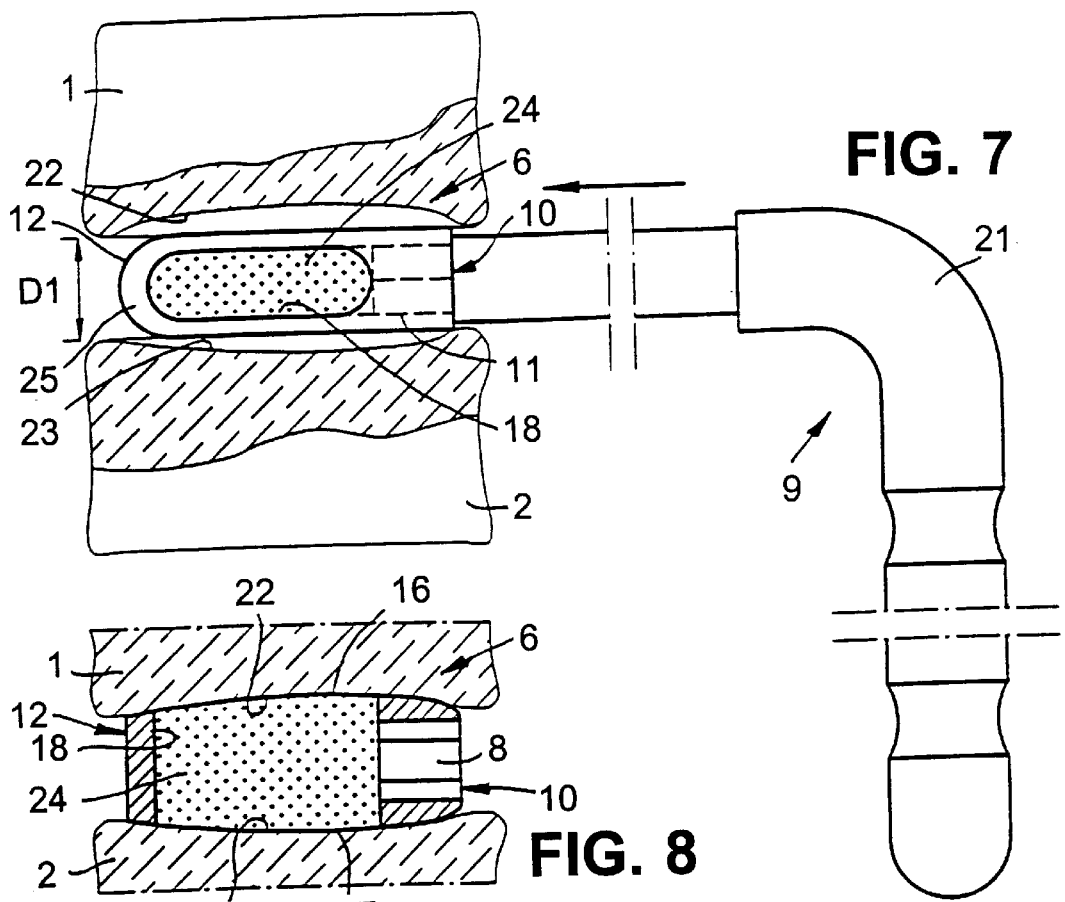
FIG. 7
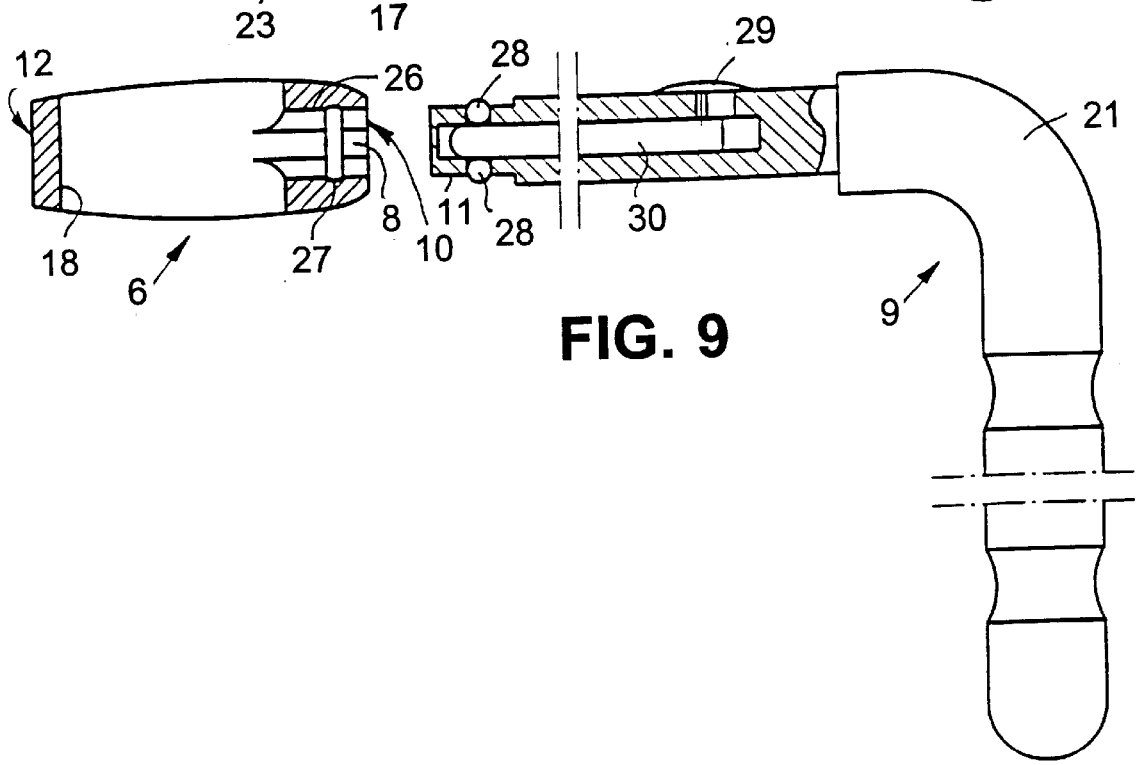
FIG. 8
FIG. 9

IMPLANT FOR INTERVERTEBRAL SPACE

This is a continuation of application Ser. No. 08/436,302, filed as PCT/CH94/00184 Sep. 20, 1994, now abandoned.

FIELD OF THE INVENTION

The invention concerns an implant for the intervertebral space. Such implants are principally intended to promote bone bridges on vertebral bodies, and are put in place following resection of disks or intervertebral disks between the vertebral body and the spinal column.

BACKGROUND OF THE INVENTION

It is known that if an intervertebral disk is damaged, it can be removed and the space thereby produced can be filled with cortico-spongiose bone.

With this method, the vertebral bodies are first spread as far apart from each other as possible using a spreader. One special technique consists of placing wedge-shaped pieces—so-called dilators—between the two vertebral bodies, to spread them in step fashion out from each other. In turn, dilators with diameters that increase in each case by 1 mm are alternately inserted from the left and right from the posterior. After the greatest possible spreading has been achieved, the dilators are replaced by the above-mentioned cortico-spongiose bone.

This known technique has a disadvantage in that the bone is difficult to manipulate and bring into the correct position, with corrections nearly impossible. An additional disadvantage of this technique is that in the intervertebral space a rectangular or cylinder-shaped recess must be cut away or milled out, to insert the bone implants between the initially concave sides of the adjoining vertebral bodies. This is complicated, and also causes damage to the vertebral body.

For this, the invention affords a remedy. The invention has the task of creating an implant for the intervertebral space. Based on its specific shape and the method of insertion, it allows an extremely stable locking between the vertebral bodies, without damaging the surface of the bony cover plate of the vertebral body.

An additional task of the invention is to create an implant for the intervertebral space which can be put in without using dilators.

SUMMARY OF THE INVENTION

The invention solves the problem with an implant for the intervertebral space which exhibits the features of claim 1, i.e., which has an essentially cuboid-shaped body with a means for gripping the body with a tool.

Additional advantageous configurations of the invention are characterized in the subsequent claims.

The implant according to the invention is equipped with a device for grasping using a tool. Therefore, an external force can be exerted on it with relatively little effort; this makes it possible to move the implant after insertion or take it out again if necessary.

The device for grasping using a tool can be configured as attachment points, so that a rotational force and/or an axial force and/or a lateral force can be exerted on the implant.

At a minimum, these attachment points are shaped in an advantageous configuration in such as way as to allow for the exertion of rotational force on the implant. The implant in this case must have different cross-sectional lengths, so that it will be squeezed to a greater or lesser extent when turned. Or, it can be placed absolutely loosely in its position, so that it can be inserted with no effort between the vertebral bodies, and demonstrate the required positional locking in another position.

In another configuration, the body of the implant in one plane has a lens-shaped, cut-to-size profile, which for the most part corresponds to the dual concave shape of the sagittal section surface of the intervertebral space. In this case the same body in the other plane has principally parallel, flat or only slightly curved sides and a rounded end, so that it can be pressed into the intervertebral space without having to cut away an insert in the vertebral body, and without damaging the edge of the vertebral body.

The implant is preferably hollow, so that it can be filled with bone material.

To better explain the invention, several examples of advantageous configurations (to which, however, the invention is not limited) are described in the following, with references to the appropriate drawings.

BRIEF DESCRIPTION OF THE DRAWINGS

In the drawings:

FIG. 7 is a schematic depiction of the implant of FIG. 3, following insertion between the vertebral bodies.

FIG. 8 is a schematic depiction of the implant of FIG. 3, following insertion between two vertebral bodies and rotation by 90°.

FIG. 9 is a schematic depiction of an alternative configuration of the invention with a tool that can be used with it.

DETAILED DESCRIPTION OF THE PREFERRED EMBODIMENTS

The invention, and additional configurations of the invention, will be described in the following in even greater detail, using the partially schematic diagrams of numerous configurational examples.

Using FIGS. 1 and 2, the known technique will first be described.

Figure 1:
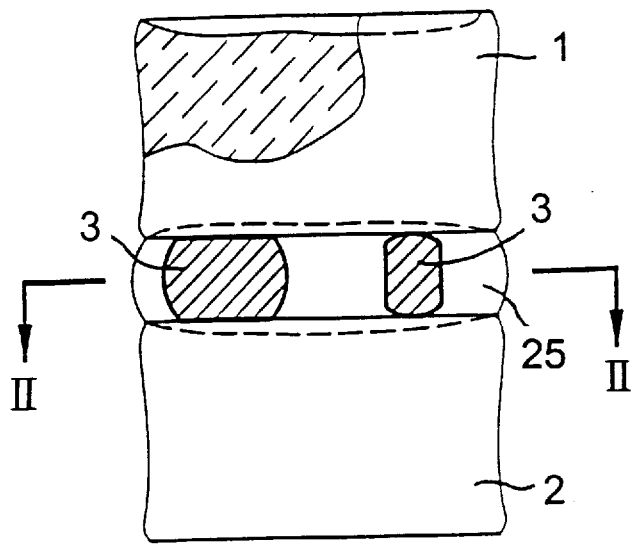
FIG. 1 is a schematic representation of two vertebral bodies, which have been spread out away from each other by two in accordance with the prior art.
Figure 2:
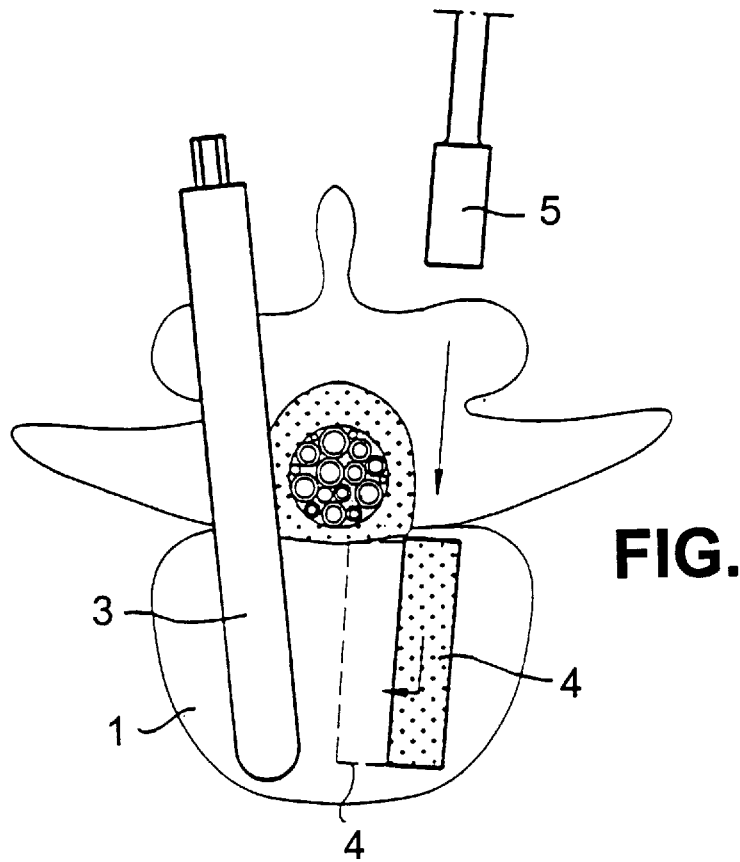
FIG. 2 is a cross section along line II—II of FIG. 1, with a dilator being replaced by a small bone cuboid.

When an intervertebral disk is removed, as FIG. 1 depicts, the two adjoining vertebral bodies 1 and 2 are spread as far away from each other as possible, so that dilators 3 can be inserted. After vertebral bodies 1 and 2 are at the desired distance. dilators 3, as depicted in FIG. 2, are replaced by the bone grafts 4. Following the cutting away of a recess in vertebral bodies 1 and 2, these bone grafts 4 must be grafted between the vertebral bodies using a pressure element. It is evident that this technique has the disadvantages, identified in the introduction to the description.

The implant according to the invention depicted in FIGS. 3–6 overcomes these disadvantages, permitting it to be inserted quickly. In addition, if necessary, it can be locked between two vertebral bodies by applying force. Implant 6 essentially consists of a body 7 with a device 8 to allow grasping using a tool 9. Device 8 for grasping using tool 9 is so configured that rotational, axial and/or lateral force can be exerted on implant 6, preferably in all directions.

Preferably, as depicted in FIGS. 3–6, device 8 is configured so that at a minimum a rotational force R can be exerted on it. In connection with that, the implant is so configured that it has differing diameters or cross-sectional lengths, so that by turning at the above-named device 8, body 7 of implant 6 can be inserted between vertebral bodies 1 and 2 at greater or lesser distances.

Device 8, as per the 3–6 configuration in FIGS. 3–6, consists of a recess made on the rear axial end 10 of implant 6, in the inner side of body 7. This recess permits tool 9 to be inserted. As shown, the recess may consist of an axially many-sided (such as hexagonal) opening. This allows tool 9 to be used, equipped with a hexagonal end 11 in the form of a socket wrench.

Use of an opening made in the inner side for inserting tool 9, such as the above-mentioned recess, offers the advantage that implant 6 has no protruding disturbing parts.

Preferably, body 7 has a particular form with one or more of the following characteristics:

The forward axial end 12 of body 7 should be configured to be rounded or wedge-shaped, since this facilitates insertion into the intervertebral space 25.

Figures 4, 6:
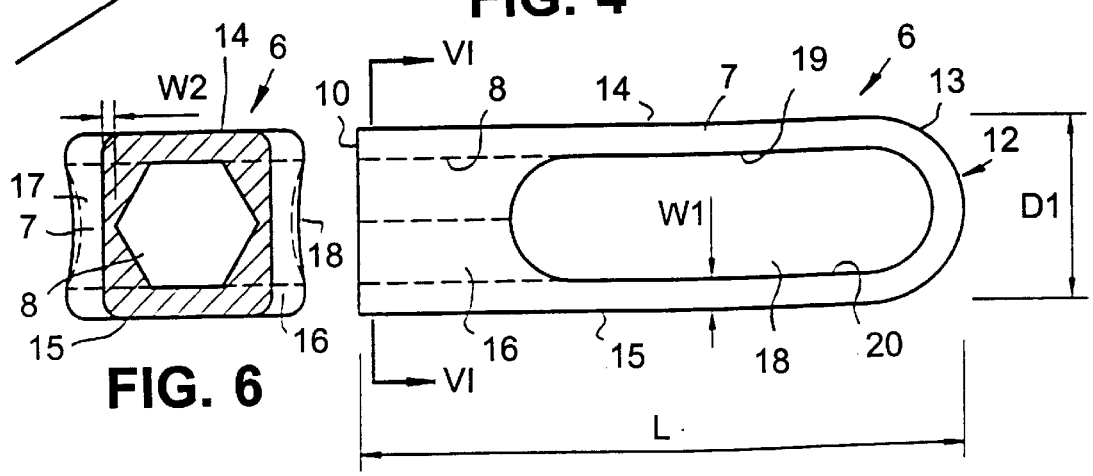
FIG. 4 is a view in the direction of arrow F4 of FIG. 3.
FIG. 6 is a cross section along line VI—VI in FIG. 4.
Figure 5:
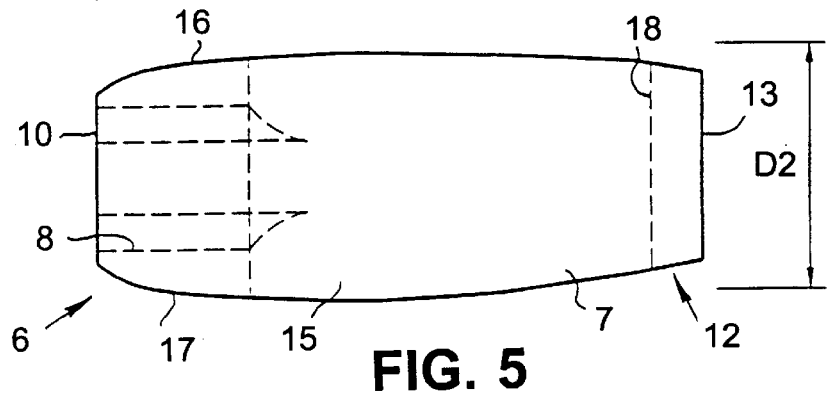
FIG. 5 is a view in the direction of arrow F5 of FIG. 3.

The rounded side 13 on the forward axial end 12 of body 7 preferably runs only along a cross section parallel to the smaller diameter Dl—see FIG. 4—and not along the cross section that is at a right angle to it, as depicted in FIG. 5.

Sides 14 and 15, through which the smaller diameter runs, are preferably parallel and flat, except for the rounded side 13.

Viewed from the side, body 7, as depicted in FIG. 5, has a rounded-off, lens-shaped profile, and thus a profile that matches the natural dual concave form possessed by an intervertebral space in the sagittal section surface. The transitions between sides 14 and 15 and sides 16 and 17 are rounded off.

Sides 16 and 17 are preferably at least partially flat, and better if completely flat, along a cross section; the fact that sides 17 and 18 in a transverse direction are at least partially flat offers the advantage that they have stability against tilt in their locked-in state.

Body 7 has one or more openings or recesses for filling with graft material. As per FIGS. 3 to 6, a straight-through opening 18, extending from side 16 to side 17, is preferred; opening 18 preferably consists of an elongated slat with parallel walls 19 and 20. The above-named recess 8 can extend to opening 18 if desired.

Preferably, the implant consists of titanium or a titanium alloy suitable for implants.

Figure 3:
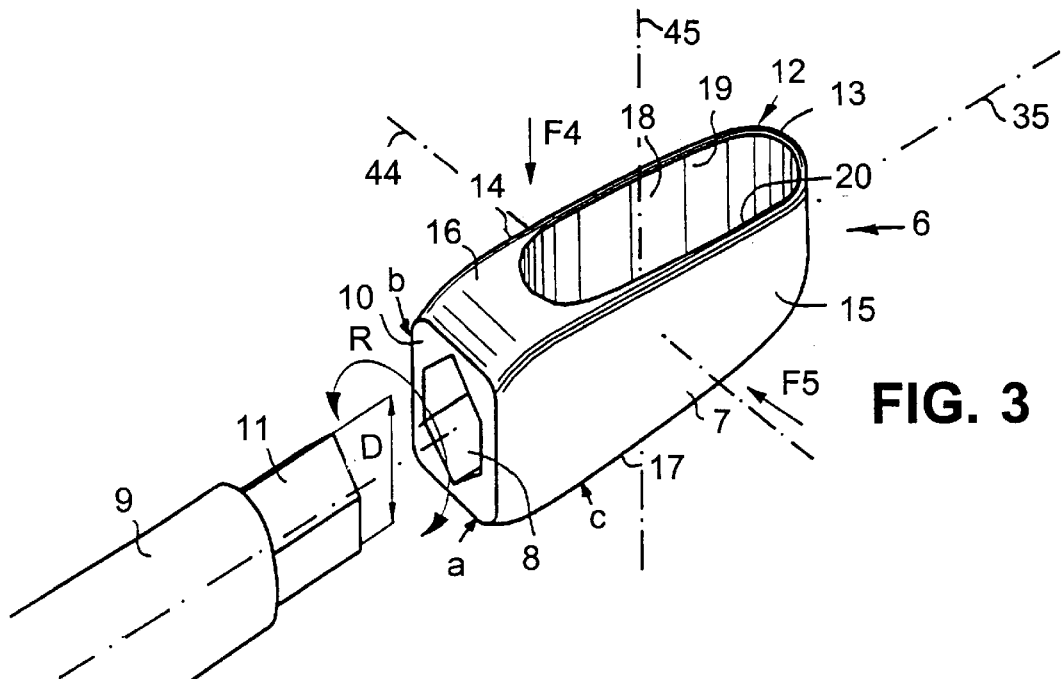
FIG. 3 is a perspective view of an implant according to the invention with a tool that can be used with it.

The opening 18 or the slat in body 7 of the implant of FIG. 3 can be made by drilling several vertical boreholes into body 7 and milling away the intermediate walls.

Preferably, implant 6, and more precisely body 7, will have a length L of about 22 mm, and will be hollowed out to an approximate wall thickness W1 of 1.5 mm. The rear axial end 10 with device 8 preferably has a minimum diameter of 6 mm. To ensure that the minimum wall thickness W2 at the site of the device 8 and the thickness D of the tool is as large as possible, the above-named recess is made so that the alignment of its greater diameter coincides with the larger diameter of body 7.

FIGS. 7 and 8 will now be used in the following to describe the use and insertion of implant 6 between vertebral bodies 1 and 2.

FIG. 7 depicts how implant 6, on the end of a corresponding tool 9 which resembles a wrench, can be inserted between the two vertebral bodies 1 and 2. Implant 6 is inserted with the smaller diameter D1 between sides 22 and 23 of vertebral bodies 1 and 2 turned toward each other. It is already filled with bone graft material 24. To insert implant 6 between vertebral bodies 1 and 2 so as to fit or lock, wrench 21 of tool 9 is turned by 90°, so that after removal of tool 9, a situation as depicted in FIG. 8 will result. Since the bone graft material 24 adjoins vertebral bodies 1 and 2, implant 6 can achieve a firm hole by coalescence of bone graft 24.

Implant 6 can be inserted with no particular auxiliary aids. However, the procedure can be simplified if the vertebrae are previously spread apart by oval dilators on the left and right side and kept in this position until an implant can be locked in place on the other side. The presence of implant 6 in turn prevents the vertebral surfaces from pressing together again. Therefore, the last dilator can be removed and, if necessary, be replaced by a second implant 6. Normally, two implants 6 must be inserted.

FIGS. 7 and 8 show clearly that with the use of a turnable implant 6 with different dimensions D1 and D2, it can be inserted between vertebral bodies 1 and 2 freely and without difficulty. In addition, it can be brought to a perfect stopping position between the two vertebral bodies by being turned. Therefore, it is not necessary to cut out or mill out the intervertebral space 25 to get a rectangular or cylinder-shaped recess.

Body 7 of implant 6 has different diameters D1 and D2. Therefore, it is easy to remove from intervertebral space 25.

It is clear that following locking in, implant 6 can be loosened by turning it in the opposite direction, until the smaller diameter D1 is between vertebral bodies 1 and 2.

If an implant 6 is used that has a body 7 possessing a shape that matches the natural dual concave shape of intervertebral space 25, a perfect fit is automatically achieved between sides 22 and 23 of vertebral bodies 1 and 2 and sides 16 and 17 of implant 6, which is grafted with bone grafts 24.

The technique of turning implant 6 has the following advantages:

If the cover plates are concave-arched, then rotation allows for the possibility of configuring implant 6 so that in one dimension it is flat, and in the other dimension it matches the geometry of the cover plates. The flat dimension facilitates insertion from the posterior direction; the arched surface affords optimal contact with the cover plates.

If the cover plates are flat, then the rotation can be used to widen the intervertebral disk space.

Transverse toothing of the surface of the implant is possible, since the implant is turned only after insertion.

Naturally, implant 6 can be designed in various shapes. In place of a recess for a hex socket wrench, other recess shapes can be used, which may, for example, be rectangular, square or oval openings.

Although device 8 for grasping using tool 9 is preferably made in the inner side of implant 4, this is not absolutely required. It can also consist of a projecting piece or of a particular configuration of the rear axial end 10, so that the projecting piece or the rear axial end 10 can be attached to a suitable tool, so that the required force can be exerted.

According to another configuration of the invention, device 8 is not exclusively designed to allow rotational force to be applied, but rather also axial force. Indeed, both a compressive and a tensile force can be exerted, so that, if necessary, implant 6, when being inserted between vertebral bodies 1 and 2 can be pressed in. If the need arises to withdraw it again, tensile force can be exerted. Thus, at any time it is possible to remove implant 6 during the operation.

Such a configuration is depicted by FIG. 9. Device 8 combines a first attachment element 26, which permits exertion of rotational force, with a second attachment element 27, which allows for the exertion of axial compression and tensile force on implant 8, and for this purpose it is equipped with an axial stop.

The first attachment element 26 consists of a recess as in the configuration depicted in FIG. 3. The second attachment element 27 consists of an additional recess, such as in the form of a slit in the wall of the above-mentioned hexagonal opening, into which the locking element 28 of the tool 9 in question can grip. As shown in FIG. 9, the locking elements 28 consist of balls or the like. After the hexagonal end 11 of tool 9 has been inserted into the hexagonal recess, these locking elements 28 press radially outwards and lock into the above-mentioned slit.

Tool 9 can have various shapes and be operated in various ways. In accordace with FIG. 9, it is controlled by means of a shifter grip 29 combined with a wedge 30, which in turn presses the locking elements away from each other or loosens them.

In another variation, not shown the wrench end is split. The exterior diameter can be increased by applying pressure or screwing an interior pin, so that the wrench can be locked into the opening of implant 6 into which it is inserted.

In still another variation, also on the front axial end 12 with the rounded side 13 of implant 6, attachment possibilities can be provided for tool 9. These attachment possibilities can be of different types, and are preferably configured so that, just as with device 8, they allow for the application of rotational force, axial force and/or lateral force onto implant 6. The attachment options consist of a many-sided (hexagonal, for example) opening, allowing insertion of a wrench with an appropriate end piece, so that torsional force can be exerted on implant 6, if it has not grown sufficiently into place and must be removed in the abdominal direction. This invention naturally also concerns to implant 6, which is equipped at one end with an attachment device that enables attachment of the implants in the abdominal direction.

Figure 10:
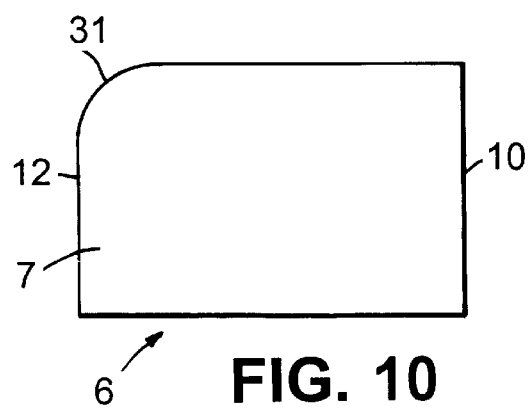
FIG. 10 is a cross section through an implant according to the invention with one rounded side.
Figure 11:
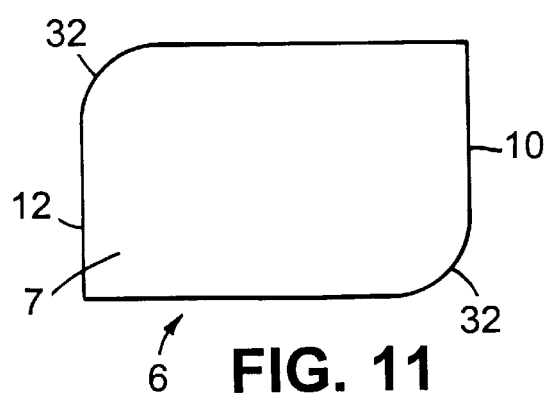
FIG. 11 is a cross section through an implant according to the invention with two sides rounded across the diagonal.
Figure 12A:
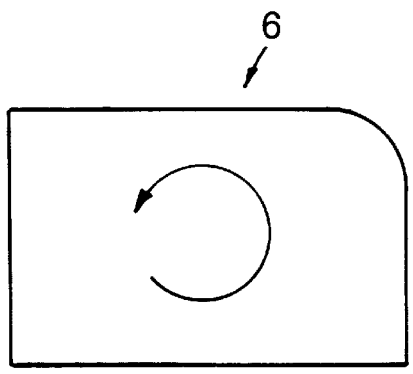
FIG. 12 is a cross section through a pairwise arrangement of two mirror-symmetric implants according to the invention.
Figure 12A:
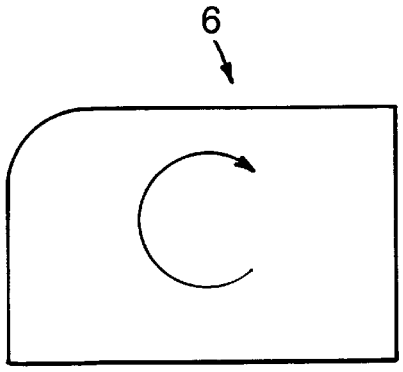
Figure 12B:
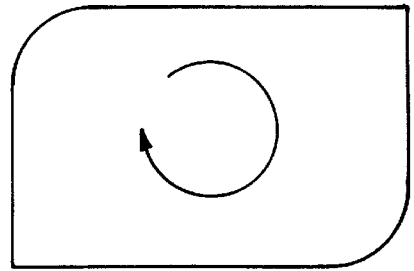
Figure 12B:
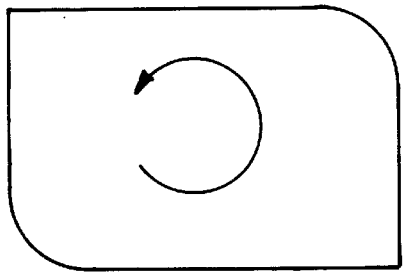

FIGS. 10 and 11 depict implants according to the invention having a partially rounded cross section.

FIG. 10 shows the body 7 of implant 6, with a rounded side 31 on the upper edge of the front axial end 12. The radius of the rounded side on one side 31 is measured in such a way that a) the difference between the larger side of the rectangular cross section and the diagonal via the rounded edge is less than 3 mm, preferably 1—2 mm. Also, b) the smaller surface is reduced by less than half, and preferably by less than a third, i.e. the carrying surface should correspond at a minimum to ⅔ of the overall width of the implant.

FIG. 11 shows the body 7 of implant 6 in cross section, with the implant having rounded sides 23 across the diagonal on each side in cross section. The radii of the opposite rounded sides 32 are measured in such a way that a) the difference between the longer side of the cross section and the diagonal across the rounded edges is less than 3 mm, preferably 0.5–1.0 mm. Also, b), the shorter side of the implant is reduced by less than half, and preferably by less than a third.

FIG. 12 depicts two pairs of implants 6, symmetrically placed along the axis of symmetry 33. The upper pair of implants 6 in section (a) are depicted as per FIG. 10, while the lower pair of implants 6 in section (b) are depicted as per FIG. 11.

When erecting (rotating) an implant as shown in FIG. 6, the intervertebral space 25 is overstretched by about 3–4 mm, which can cause the cover plates to break and can lead to permanent overstretching of the connective tissue. If the edges are rounded (31, 32), overstretching is greatly reduced, but this, however, reduces the stability of the straightened implants. Or, the paired implants are arranged to be mirror-symmetric, to mutually stabilize each other (see FIG. 13).

Figure 13:
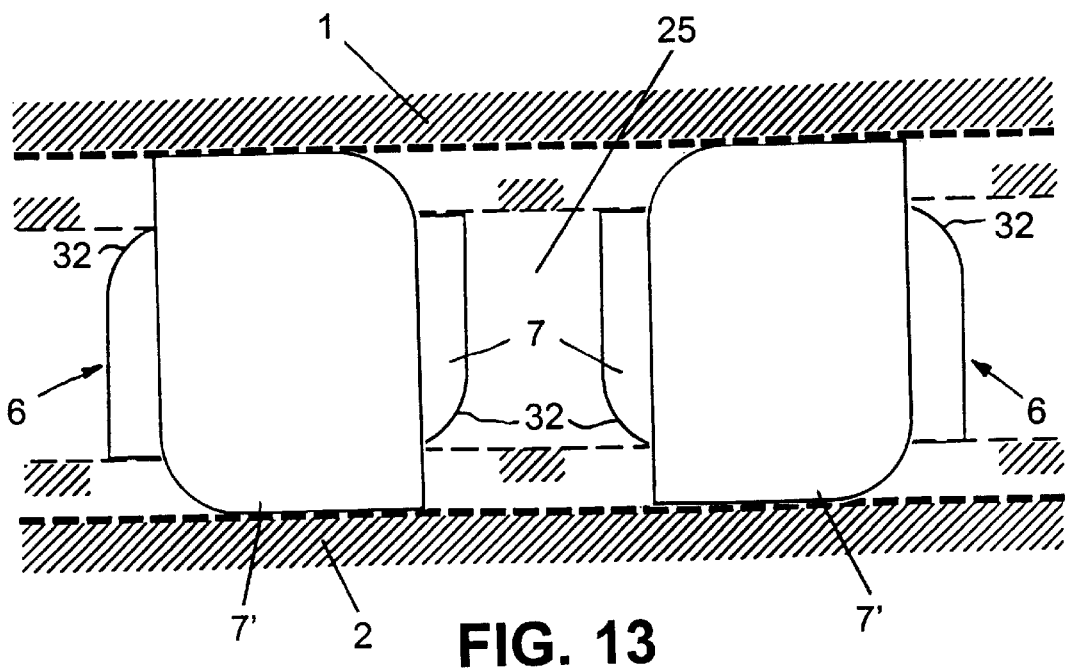
FIG. 13 is a schematic depiction of pairwise arranged, mirror-symmetric implants, according to the invention, through whose use the intervertebral disk space can be widened.

Erection using two implants 6 which have rounded sides 31 and 32 with suitably selected radii, results in overstretching of the intervertebral space by only 1 mm. However, the individually set up implants 6 are not too stable. They can tilt back as easily as they were erected. In FIG. 13, the two implants 6 are mutually protected by their mirror-symmetric geometry from tilting, since the implants 6 can tip only as a pair and not individually.

FIG. 13 shows two mirror-symmetrically arranged implants 6 in accordance with FIG. 11. The rounded sides 32 of body 7 lie symmetrically to each other. Following insertion, the bodies 7 of implants 6 lie horizontally between vertebral bodies 1 and 2. They can then be rotated using a suitable tool 9 by 90° into the position 7' drawn in black, to expand the intervertebral space 25. The rectangular cross section of body 7 is created in such a way that following rotation of implant 6 by 90°, into the concave space of the cover plates of the adjoining vertebral bodies 1 and 2, there is a residual widening of the intervertebral space 25 of between 1 and 4 mm, preferably between 2 and 3 mm.

Figure 14:
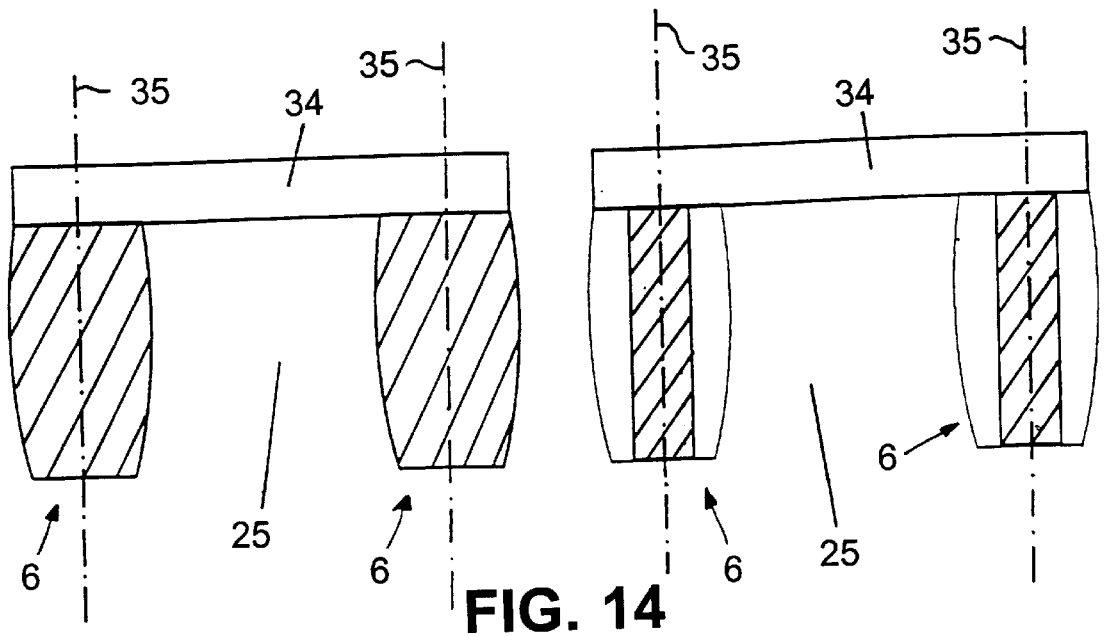
FIG. 14 is a schematic depiction of two implants lying flat in the intervertebral disk space. These two implants are connected anteriorly by a third implant, before and after rotation into the concave area of the cover plates of the adjoining vertebral bodies.

FIG. 14 shows two implants 6, lying flat in intervertebral space 25 (plane of the drawing). These are linked in anterior fashion with each other by a connector 34. The left side of FIG. 14 depicts the position before rotation of implant 6. The right side of FIG. 14 shows the placement after rotation by 90° into the concave area of the cover plates of adjoining vertebral bodies.

The posterior end of implant 6 remains free, and is linked only by connector 34 in anterior fashion, so that (a) the distance between the right and left implant 6, and their orientation, is kept in place. Also (b), implants 6 are able to be turned about their longitudinal axis 35. In addition (c), the two implants 6 can be coupled prior to implantation and/or in situ by connector 34.

Figure 15:
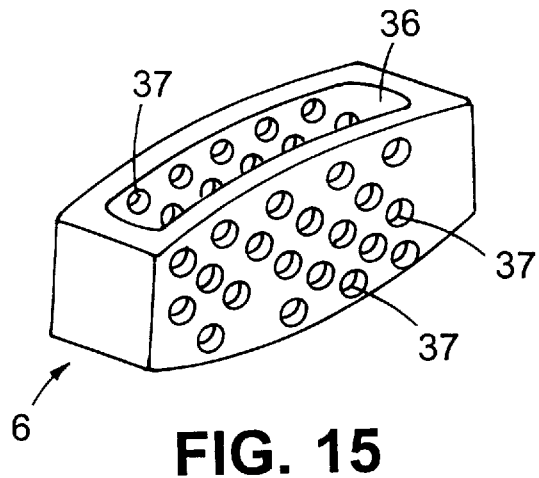
FIG. 15 is a perspective view of an implant according to the invention with a longitudinal cut to admit spongy bone material or osteoconductive or osteoinductive material, and transverse perforation of the walls for bone growth.

FIG. 15 shows an implant 6 with a longitudinal cutout 36 to admit spongy bone material or osteoconductive or osteoinductive material. It also has transverse perforations 36 of its walls for bone growth. Preferably, the diameter of perforations 36 is designed in such a way that (a) cancellous bone pressed into longitudinal cutout 36 does not escape from the sides. Also (b) upon filling implant 6, the fluid contained in the cancellous bone is able to escape out the sides and then diffuse back following implantation, to effect a postoperative swelling of the cancellous bone. Also (c), bone can grow into implant (6) through the perforations 37.

Figure 16:
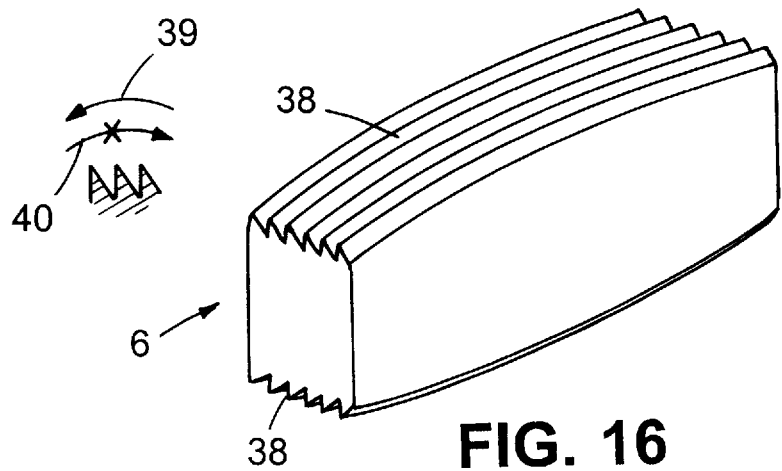
FIG. 16 is a perspective view of an implant according to the invention with longitudinally toothed contact surfaces between implant and bone. The longitudinal toothing is configured so that rotation of the implant into the concave space of the cover plates is possible only in one direction.

FIG. 16 shows an implant 6, whose contact surfaces between implant 6 and the bone are equipped with a longitudinal toothing 38. The longitudinal toothing 38 is preferably configured in such a way that rotating the implant 6 into the concave space of the cover plates is possible only in one direction, as indicated by arrows 39, 40.

Figure 17:
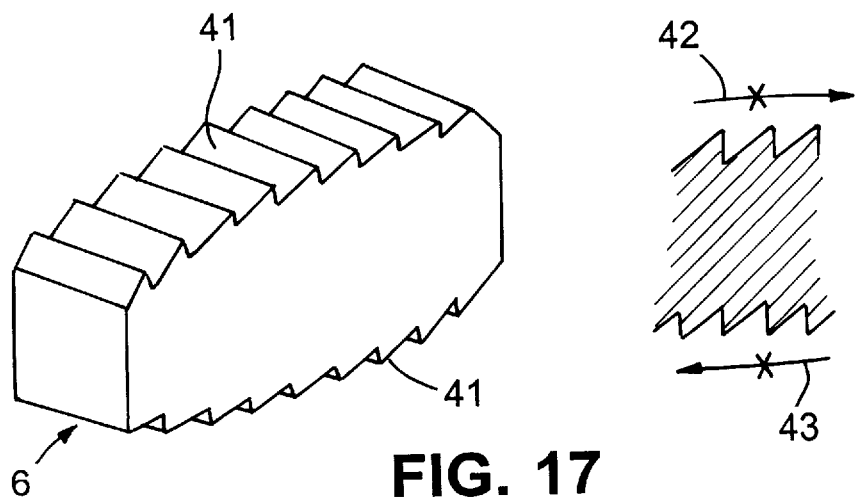
FIG. 17 is a perspective view of an implant according to the invention with transversely toothed contact surfaces between implant and bone. The transverse toothing is configured so that one toothing prevents translational motion in the anterior direction, while the other toothing prevents translational motion in the posterior direction. Preventing translational motion in the anterior direction results in pressure removal from the remaining annulus, which, according to the latest research, is innervated, and may react with pain signals to anterior pressure.

FIG. 17 shows an implant 6 whose contact surfaces between implant 6 and the bone are equipped with a transverse toothing 41. Preferably, the transverse toothing 41 is configured in such a way that it prevents the one contact surface from making translational motion in the anterior direction, while it prevents the other contact surface from making a translational motion in the posterior direction, as shown by arrows 42, 43. Prevention of translation in the anterior direction causes a removal of pressure on the remaining annulus, which, according to the latest research, is innervated, and thus could react with pain signals to anterior pressure.

In no way is this invention limited to the examples given and the models depicted in the illustrations. Such dilators and the accompanying tool can take various shapes and sizes.

What is claimed is:

1. An implant for an intervertebral space formed between cover plates of adjoining vertebrae, said implant comprising essentially a cuboid-shaped body having a device for gripping a tool wherein said device is adapted to allow for the application of a rotational force on said implant in either rotational direction around a longitudinal axis through said implant and for removable insertion of said tool and further wherein said body comprises a plurality of openings for filling with graft material, said plurality of openings being arranged such that when filled with graft material, said graft material contacts the cover plates when said implant is in position in the intervertebral space.

2. The implant according to claim 1 wherein the device comprises a many sided recess into the body, into which a tool can be inserted.

3. The implant according to claim 2 wherein the recess comprises an interior hexagon.

4. The implant according to claim 1 wherein the device is adapted to allow for application of an axial, compressive or tensile force on the implant.

5. The implant according to claim 2 wherein the recess is adapted to admit a tool and wherein the recess contains two attachment elements for locking the tool.

6. The implant according to claim 1 wherein the device is adapted to allow for the application of lateral force on said implant.

7. The implant according to claim 1 having horizontal side portions which are predominantly parallel and flat.

8. The implant according to claim 7 having vertical side portions which have at least a partially rounded-off, lens-shaped profile.

9. The implant according to claim 1 wherein at least one of its axial ends is rounded off.

10. The implant according to claim 1 which is provided with a straight-through opening, having the shape of an elongated groove with parallel walls.

11. The implant according to claim 1 having a second device for gripping a tool.

12. The implant according to claim 1 which comprises titanium or a titanium alloy.

13. The implant according to claim 1 which has a substantially rectangular cross section with one side rounded.

14. The implant according to claim 13 wherein the radius of the one rounded side is such that
    (a) the difference between a longer side of the periphery of the rectangular cross section and a diagonal across the rounded edge is less than 3 mm; and
    (b) because of the rounded side, the implant surface which contacts bone is reduced by less than half.

15. The implant according to claim 1 which has a substantially rectangular cross section with two rounded sides across a diagonal of the rectangle.

16. The implant according to claim 15 wherein the radii of the two rounded sides are such that
    (a) the difference between a longer side of the periphery of the cross section and a diagonal across the rounded edges is less than 3 mm; and
    (b) a smaller surface of the implant is reduced by less than half.

17. A pair of the implants according to claim 15 which share the same intervertebral space arranged such that their respective rounded sides lie symmetrically to each other.

18. The implant according to claim 15 which is arranged in such a way that after a rotation of the implant in the space between the cover plates, a widening of the intervertebral space of between 1 and 4 mm remains.

19. The implant according to claim 15 which has a substantially square cross section such that after a rotation of the implant in the space between the cover plates, substantially no widening of the intervertebral space remains.

20. The implant according to claim 15 having a surface which is coated.

21. The implant according to claim 1 wherein the openings are in two bone contacting surfaces of said implant and the size of the openings is such that bone can grow through the openings and into the implant.

22. The implant according to claim 15 which in use has at least one contact surface between the implant and a cover plate, and said contact surface has toothing in the longitudinal direction of the implant.

23. The implant according to claim 15 which in use has two contact surfaces between the implant and the cover plates, and the contact surfaces have toothing in the longitudinal direction of the implant.

24. The implant according to claim 22 in which the toothing permits rotation of the implant in a first direction and prevents it in a second direction.

25. The implant according to claim 15 which in use has at least one contact surface between the implant and a cover plate, and said contact surface has transverse toothing.

26. The implant according to claim 15 which in use has two contact surfaces between the implant and the cover plates, and the contact surfaces have transverse toothing.

27. The implant according to claim 25 in which the toothing prevents displacement of the implant in the anterior direction.

28. The implant according to claim 25 in which the toothing prevents displacement of the implant in the posterior direction.

29. The implant according to claim 26 in which the toothing of the contact surfaces between the implant and the cover plates is configured in such a way that one toothing prevents a displacement of the implant in the anterior direction, and the other toothing prevents a displacement in the posterior direction.

30. The implant according to claim 22 which also has a second contact surface, which second contact surface has transverse toothing.

31. The implant according to claim 10 wherein the walls have transverse slots.

32. The implant according to claim 31 wherein the slots are filled with an osteoconductive or osteoinductive material.

33. An implant for an intervertebral space formed between cover plates of adjoining vertebrae, said implant comprising essentially a cuboid-shaped body having a substantially rectangular cross section with two rounded sides across a diagonal of the rectangle, posterior and anterior ends wherein the posterior end of the implant is designed such that a second implant can be connected anteriorly to the implant by a connector, and a device for gripping a tool wherein said device is adapted to allow for the application of a rotational force on said implant in either direction around a longitudinal axis through said implant and further wherein said body comprises a plurality of openings for filling with graft material, said plurality of openings being arranged such that when filled with graft material, said graft material contacts the cover plates when said implant is in position in the intervertebral space.

34. An implant for an intervertebral space formed between cover plates of adjoining vertebrae, said implant being designed such that it can be interlocked with a second implant either prior to being implanted or while in situ, and said implant comprising essentially a cuboid-shaped body having a substantially rectangular cross section with two rounded sides across a diagonal of the rectangle, and a device for gripping a tool wherein said device is adapted to allow for the application of a rotational force on said implant in either direction around a longitudinal axis through said implant and further wherein said body comprises a plurality of openings for filling with graft material, said plurality of openings being arranged such that when filled with graft material, said graft material contacts the cover plates when said implant is in position in the intervertebral space.

35. An implant for insertion and rotational locking in an intervertebral space formed between cover plates of adjoining vertebrae, said implant comprising a generally cuboid-shaped body having major, minor and median length axes of differing dimensions, said body having external surfaces intersecting said axes, a device for coupling with a tool, said device being located adjoining one of said surfaces of said body intersecting said major axis, wherein said device is adapted to allow for the application of a rotational force on said implant in either rotational direction around said major axis through said implant and for uncoupling of said tool, and at least one opening located in each of said surfaces intersecting said median axis.

36. The implant of claim 35 wherein said surfaces intersecting said median length axis are convexly curved in the direction of the longitudinal axis.

37. The implant of claim 35 wherein said surfaces intersecting said minor axis are flat.

38. The implant of claim 35 further comprising a slot extending continuously between said surfaces intersecting said median axis to permit the formation of an uninterrupted bony bridge between said cover plates therein.

* * * * *

UNITED STATES PATENT AND TRADEMARK OFFICE
CERTIFICATE OF CORRECTION

PATENT NO. : 5,888,224
DATED : MARCH 30, 1999
INVENTOR(S) : LOUIS FRANCOIS CHARLES BECKERS & JOHANNES FRIDOLIN SCHLAPFER

It is certified that error appears in the above-indentified patent and that said Letters Patent is hereby corrected as shown below:

Col. 2, line 26, after "two" insert --dilators--.

Col. 4, line 16, after "elongated" change "slat" to --slot--;

Col. 4, line 21, after "or the" change "slat" to --slot--.

Col. 6, line 31, change "third" to --quarter--.

Signed and Sealed this

Twenty-seventh Day of March, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 5,888,224
DATED : March 30, 1999
INVENTOR(S) : Louis Francois Charles Beckers, Johannes Fridolin Schlapfer It is certified that error appears in the above-identified patent and that said Letters Patent is hereby corrected as shown below:

TitlePage,
The Assignee "Synthesis (U.S.A.)" should be -- Synthes (U.S.A.) --.

Signed and Sealed this

Fourteenth Day of August, 2001

*Attest:*

*Attesting Officer*

NICHOLAS P. GODICI
*Acting Director of the United States Patent and Trademark Office*